United States Patent [19]

Forberg et al.

[11] 4,009,715
[45] Mar. 1, 1977

[54] FILTER FOR INFUSION AND TRANSFUSION APPARATUS

[75] Inventors: Hans-Jürgen Forberg, Lensahn, Holst; Hans-Joachim Haese, Thomstorf; Herbert Mänz, Neustadt, Holst, all of Germany

[73] Assignee: Transcodan Sven Husted-Andersen, Germany

[22] Filed: Aug. 22, 1975

[21] Appl. No.: 606,978

[30] Foreign Application Priority Data

Aug. 29, 1974 Germany .......................... 2441329
Mar. 8, 1975 Germany .......................... 2510148

[52] U.S. Cl. .................... 128/214 R; 210/DIG. 23; 210/455
[51] Int. Cl.² ........................................ A61M 5/16
[58] Field of Search ........ 128/214 R, 214 C, 214.2, 128/221; 210/DIG. 23, 304, 455, 498; 55/159

[56] References Cited

UNITED STATES PATENTS

| 2,646,678 | 7/1953 | Standing et al. | 210/455 |
| 3,386,585 | 6/1968 | Weyand et al. | 210/455 X |
| 3,556,302 | 1/1971 | Agranat | 210/321 |
| 3,650,093 | 3/1972 | Rosenberg | 128/214.2 |
| 3,730,353 | 5/1973 | Trasen et al. | 210/455 |
| 3,815,754 | 6/1974 | Rosenberg | 210/445 |
| 3,905,905 | 9/1975 | O'Leary et al. | 210/436 |

Primary Examiner—Dalton L. Truluck
Attorney, Agent, or Firm—McGlew and Tuttle

[57] ABSTRACT

A filter particularly for infusion and transfusion apparatus, comprises a housing having an inlet passage and a discharge passage spaced from the inlet passage. The housing includes a surface with a spiral flow passage defined thereon which is centrally communicated to the discharge passage. A filtering material is placed over the spiral in the housing which is made up of two parts which are interconnectable at the location of the spiral and which also act to hold the filter material in position. In an alternate embodiment, the housing of the filter is formed as a portion of a cannula. The inlet and outlet flow passages of the housing may be arranged to align axially, for example, on one side of the housing, or they may be offset.

16 Claims, 7 Drawing Figures

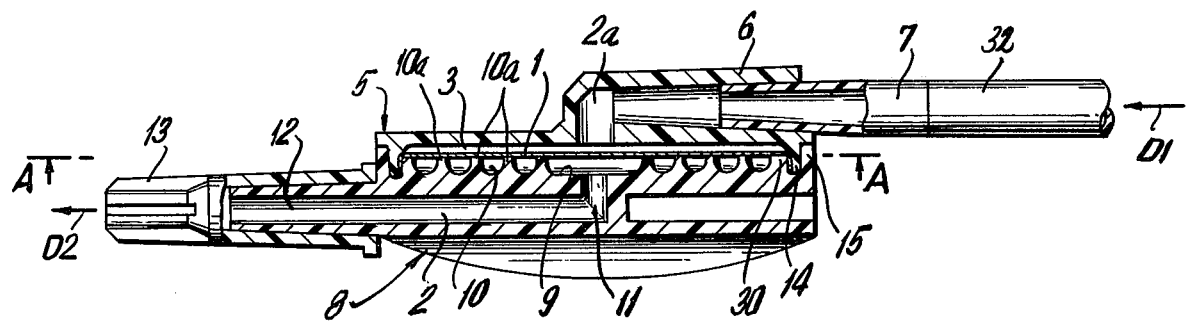
FIG. 1
FIG. 2
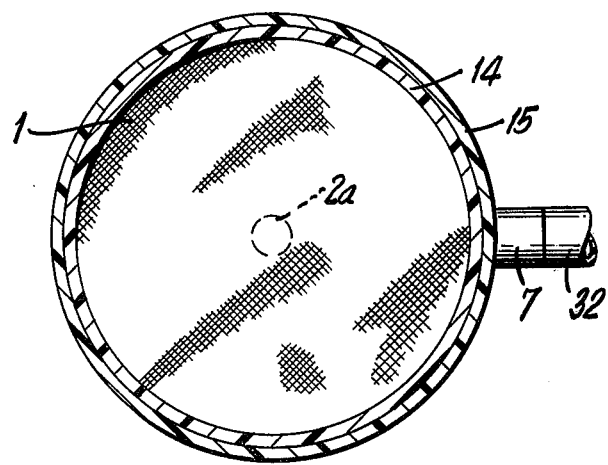
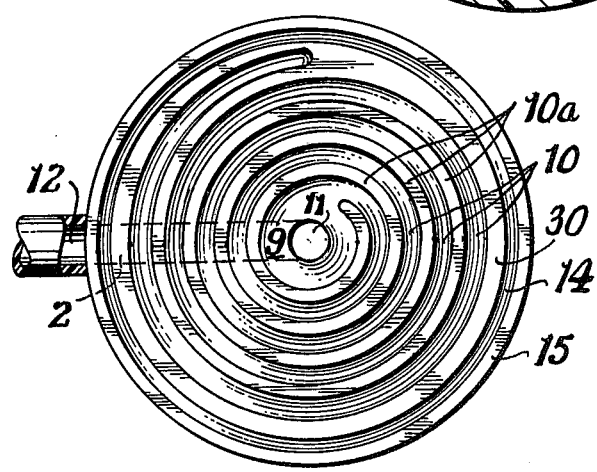
FIG. 7

FILTER FOR INFUSION AND TRANSFUSION APPARATUS

FIELD AND BACKGROUND OF THE INVENTION

This invention relates in general to the construction of filters and, in particular, to a new and useful transfusion and infusion apparatus having a filter which includes a housing having an inlet passage and a discharge passage and a spiral flow passage between the inlet and discharge which is covered by a filtering material disposed between the spiral passage and the inlet and the outlet passage communicates with the central portion of the spiral.

DESCRIPTION OF THE PRIOR ART

It is usual to mount filters in the flow path of infusion and transfusion apparatus in order to filter off or intercept any particles which may have passed into the liquid stream. Such particles may be sediments of the solutions, germs, or the like. The filters produce a resistance so that the solution to be filtered must be pressed through the filter under a certain overpressure. To reduce the resistance, the filter is designed with a large cross-section relative to the normal cross-sections of the conduits of the apparatus. This requires the housings for the reception of the filters to be constructed with correspondingly large cavities both at the inlet and the outlet side of the liquid stream. Such cavities have a cross-section corresponding at least to the extension of the filter, for example, with circular filters, it would correspond to the filter diameter.

During operation of the filter, the liquid must flow through the cavities so as to completely expel the air. Otherwise, with a disorderly venting, air bubbles may remain in the housing and this would reduce the filtering surface, and this would further increase the resistance of the filter. In addition, during the infusion and transfusion, air bubbles may be entrained from the air space behind the filter. From the air space of the housing before the filter, even after the filter has been wetted, air can no longer pass through the filter. For these reasons, the operator must handle the housing of the filter skillfully by turning the housing in a manner so as to expel the air from the housing. This is a disadvantage.

SUMMARY OF THE INVENTION

The present invention provides a filter which is mounted in the liquid flow path of an infusion and transfusion apparatus in which the disadvantages of the prior art are avoided and which is designed so that, in operation, the air is securely and completely removed from the conduits and the filter.

In accordance with the invention, the housing includes at part at the outlet side which is designed as a spiral with an opening centrally of the spiral into the discharge. The inventive filter has the advantage that at the side of the liquid outlet, the air is positively displaced from the cavities and leaves the filter housing in the direction of the liquid outlet along with the flowing fluid. The air is then evacuated through the line. Thus, the air cannot settle in the lower part of the filter housing and the danger of an intermittent occurrence of bubbles in the outlet line of the filter is eliminated.

In a simple embodiment of the invention, the filter rests directly against the edges of a grooved wall defining a spiral passage or recess on the surface of one of the housing parts. This housing part is provided with an outlet conduit which connects centrally into the spiral groove. A second housing part interfits over the first housing part and includes a wall which is spaced from the groove forming the spiral passage to define a cavity or clearance space. The cavity is dimensioned so that the flowing liquid is able to expel the air uniformly and rapidly. Thereby, the filtering surface is prevented from becoming unnecessarily reduced by an improper venting. Should air bubbles incidentally accumulate at this side during the infusion, there is virtually no danger of air being pressed through the filter which is wetted by the liquid and, thereby, will not pass into the outlet line of the liquid. Thus there is no danger that the infusion or transfusion will be stopped.

In a simple embodiment, the housng part is provided with an inlet connection for the liquid which has a bore opening into the inner surface of the housing part, preferably centrally of the wall which is spaced from the wall defining the grooves of the spiral passage. This simplifies the construction and makes it possible to make an extremely small clearance space.

The inventive structure may be further simplified by providing the rims of the joining surfaces of the two housing parts with interengaging connecting means, such as a tongue-and-groove joint and/or by welding this joint. This results in a structurally very simple and effective filter.

In accordance with a further development of the invention, the housing is designed as a cannula or as a cannula holder. The construction may comprise a wing-type cannula holder or a part of the cannula itself. The construction has the advantage of permitting easy manipulation of the filter and the cannula, and it makes the overall construction very simple and inexpensive. In order to facilitate the expelling of the air from the transfusion and infusion liquid, the interior of the housing may include a plate on the covering housing part which rests against the inner surface of this housing part and is spaced only slightly from the spiral flow surface and the filter of the other housing part.

In a still further embodiment of the invention, the housing is provided with an attachment forming a neck extension which is closed by a piercable cap which affords a connection for an additional liquid or medicament which may be directed into the inflow transfusion or infusion liquid. The attachment includes a conduit for connecting a syringe which terminates in a liquid conduit leading to the filter. The attachment is advantageously mounted perpendicularly to the contact surface of the cannula holder.

Accordingly, it is an object of the invention to provide a filter particularly for tranfusion and infusion apparatus which comprises a housing having an inlet passage and a discharge passage with a surface between the inlet and discharge passages defining a spiral flow passage having a filter between the spiral flow passage and the inlet and, wherein, the outlet communicates centrally with the spiral flow passage.

A further object of the invention is to provide an infusion and transfusion apparatus which includes an infusion conduit having a filter therein which includes a housing having a widened portion with a spiral passage defined in the surface thereof with an inlet and outlet connected to respective sides of the spiral passage which includes a filter material disposed between the spiral passage and the inlet.

A further object of the invention is to provide a filtering device which also comprises a cannula or cannula holder and which may be equipped with an attachment for inserting an additional medicament or liquid into the infusion or transfusion flow stream.

A further object of the invention is to provide a filtering device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there are illustrated preferred embodiments of the invention.

BRIEF DESCRIPTION OF THE DRAWINGS

In the drawings:

FIG. 1 is an axial sectional view of a filter housing constructed in accordance with the invention;

FIG. 2 is a section taken along the line A—A of FIG. 1;

FIG. 7 is a partial top plan view of the bottom portion of the housing shown in FIG. 1 indicating the spiral groove.

DESCRIPTION OF THE PREFERRED EMBODIMENTS

Figure 3:
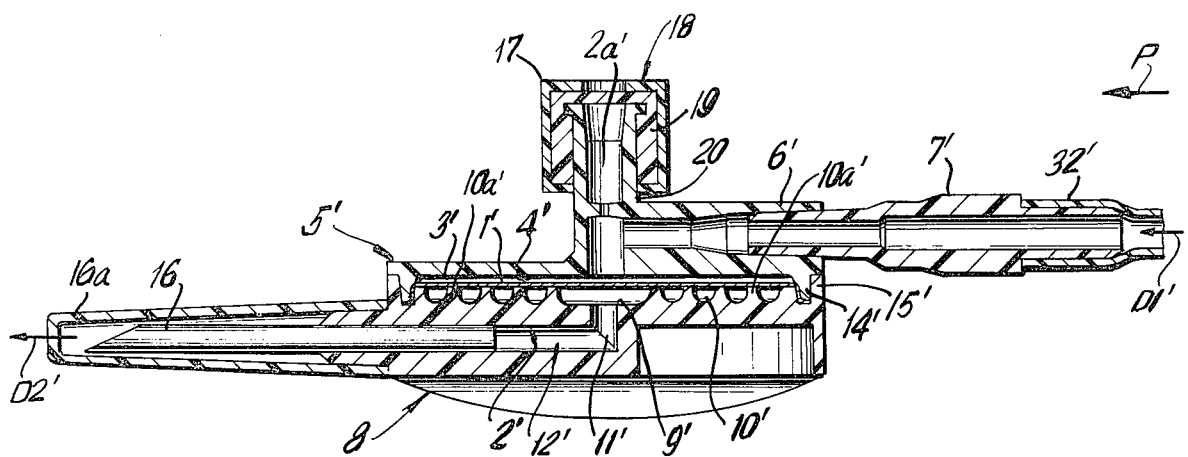
FIG. 3 is a sectional view, similar to FIG. 1, of another embodiment of the invention.

Referring to the drawings in particular, the invention embodied therein in FIGS. 1 and 2, comprises an infusion or transfusion apparatus with a flow line or conduit 7 through which an infusion or transfusion substance flows in the direction of the arrow D1 into an inlet fitting 6 of an upper or first housing part 5 and through a central conduit 2a of the housing into a clearance space 3 which is situated above a filtering material 1.

In accordance with a feature of the invention, the upper housing part 5 is interengaged with a lower housing part 8 which has an outlet fitting 12 connected to the downstream section 13 of the infusion or transfusion apparatus for further flow in a direction indicated by the arrow D2. Inlet connection 6 is provided with an inward taper sized to engage a similarly tapered end portion of the infusion and transfusion conduit 7. Housing part 8 has a surface 9 of relatively large diameter in respect to the diameter of the outlet conduit 12 and inlet conduit portion 2a. A spiral-shape recess 10 is defined on surface 9 and it communicates at its central portion with the orifice or bore 11 of the outlet conduit 12. The spiral-shape recess 10 is formed by separating upstanding web portions 10a and by an outer annular web portion 30. Upper housing part 5 includes an annular flange 14 which fits over the annular portion 30 and engages and holds the outer periphery of the filtering material 1. The flow of the infusion or transfusion substance is directed through a flexible conduit 32, the fitting 7 and the inlet 6 through the bore 2a and the space 3 through the filter material 1 and through the spiral recess 10 to the center of the spiral recess and through the bore 11 communicating therewith and out through the outlet conduit 12. In the drawing, the outlet conduit is shown as being covered by a stopper or protective cap 13 which may be removed to permit connection of the outlet conduit to a flexible tubing.

Preferably, the tops of all of the web portions 10a are in contact with the filter material 1. As soon as the liquid flows through the filter in the direction of the arrow D1, the air present in the inlet bore 2a for the liquid, as well as the air present in the clearance space 3, is pressed through filter 1. The filter is dimensioned so that the liquid is distributed rapidly and uniformly thereby displacing the present air from the clearance space 3, prior to wetting the filter material. The air present in the spiral-shape space formed between the surface of filter material 1 and the bore 11 is thrust by the inflowing liquid to the central space 9 of the spiral passage and into the bore 11 and is evacuated out the outlet bore 12 along with the liquid in the direction of the arrow D2.

The bottom housing part 8 is also advantageously provided with an annular portion forming an interengaging connection with the portion 15 and these portions may be, for example, interfitting groove-and-tongue joints and, in addition, they are advantageously welded together.

Figure 4:
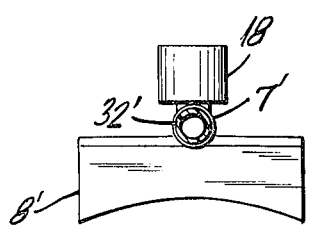
FIG. 4 is an end elevational view of the embodiment shown in FIG. 3 taken in the direction of the arrow indicated P.

In the embodiment indicated in FIGS. 3 and 4, similar parts are similarly designated, but with primes. In this embodiment, an upper housing part 5' includes an attachment, generally designated 18, which forms a neck 20 extending upwardly above the inlet passage 2a which defines a passage which communicates with the passage 2a and which is closed by a cap 17 which fits over a piercable top piece 19. Cap 17 has an opening for a syringe which may be pierced into the piercable part of the inner portion 19 to permit the adding of a medicament or other material into the flow stream designated D1'.

In accordance with another feature of the construction of FIGS. 3 and 4, a housing part 8' forms a cannula or a cannula holder for a cannula 16 which is covered by a cap 16a. This part also forms a spiral recess 10' between upstanding web portions 10a' which are covered by filtering material 1' leaving a space 3' between filter 1' and the interior surface 4' of housing part 5'. Housing part 8' includes an interior bore 2' forming the interior of the cannula 16 and which connects to the bore 12' and central bore 9' at the center of the spiral for outward flow in the direction of the arrow D2'. The upper edges of the webs 10a' rest directly against the surface of the filtering element 1'. The construction shown in FIG. 1 may be made of a single housing part or the two housing parts as indicated.

Figure 5:
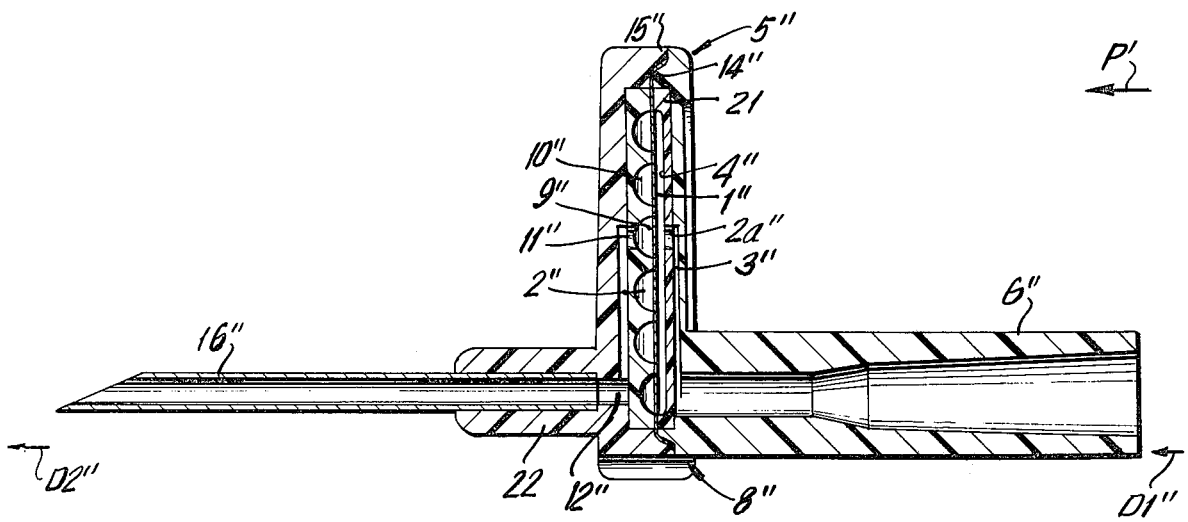
FIG. 5 is a sectional view similar to FIG. 1 of still another embodiment of the invention.
Figure 6:
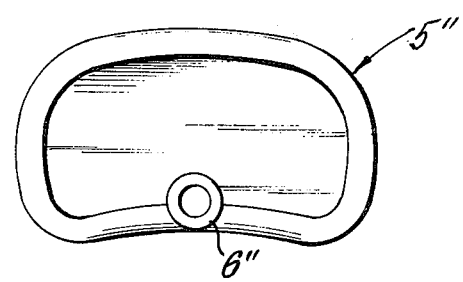
FIG. 6 is an end elevational view taken in the direction of the arrow P' of FIG. 5.

In the embodiment of FIGS. 5 and 6, similar parts are similarly designated, but with double primes. In this embodiment, the housing parts 5'' and 8'' together form the holding plate of a cannula holder. The filter 1'' may be circular or adapted to the shape of the holding plate. Housing part 5'' is provided with a liquid inlet connection 6'' extending perpendicularly to the housing part, and housing part 8'' is provided with a connection 22 for the cannula 16'' which is aligned axially with the connection 6''. The flow directions are indicated by the arrows D1'' and D2''.

While specific embodiments of the invention have been shown and described in detail to illustrate the application of the principles of the invention, it will be understood that the invention may be embodied otherwise without departing from such principles.

What is claimed is:

1. A filter particularly for transfusion and infusion apparatus, comprising a housing having an inlet passage, a discharge passage, and a single closed continuous spiral flow passage between said inlet passage and said discharge passage, a filtering material located between said spiral passage and said inlet, said outlet passage communicating with the center of said spiral passage.

2. A filter according to claim 1, wherein said housing has a wide surface in which said spiral passage is defined with a central groove of at least twice the passage width having a bottom opening communicating with said outlet passage, said housing having successive spiral coil upstanding web portions between passage portions having tops which are engaged with said filter.

3. A filter according to claim 1, wherein said housing is shaped to define a clearance space over said filter communicating centrally with said inlet.

4. A filter comprising a housing having first and second housing parts each having a substantially cylindrical shallow depth portion, said first housing part having a surface with a single closed continuous spiral groove defined therein and a central opening, a first flow passage defined in said first housing part communicating with said opening, said second housing part having a cylindrical portion interengaged with said first housing part around the periphery of said spiral passage and a filter disposed between said spiral passage and said second housing part, said second housing part having an inlet passage communicating centrally to the space above said filter.

5. A filter according to claim 4, wherein said housing parts have annular rim portions surrounding the spiral passage which are interengaged.

6. A filter according to claim 5, wherein said rim portions include interengaged groove-and-tongue portions.

7. A filter according to claim 5, wherein said filtering material is engaged over the outer boundary wall of the spiral passage and is held thereby peripherally by interengagement of said first and second housings.

8. An infusion and transfusion apparatus, comprising a flow conduit having a filter housing therein, said filter housing including a large wall surface having a single closed continuous spiral-shape groove passage defined therein with upstanding web portions defined between portions of said passage and including a central opening communicating with said transfusion passage, a filter stretched over said web portions and an inlet passage for the transfusion and infusion material connected to the opposite side of said filter.

9. A filter according to claim 4, wherein one of said first and second housing parts comprises a holder for a cannula.

10. A filter according to claim 4, wherein said first housing part has a holding portion communicating with said first flow passage and including a cannula mounted on said holding portion and communicating with said first flow passage.

11. A filter according to claim 10, wherein said inlet passage and said flow passage are aligned axially.

12. An infusion and transfusion apparatus, according to claim 8, including a cannula mounted on said filter housing and communicating with said central opening.

13. An infusion and transfusion apparatus, according to claim 8, including an attachment on said housing having a closable opening communicating with said inlet passage for the addition of a material into the infusion and transfusion liquid.

14. A cannula, comprising a housing having an inlet connection and a discharge connection separated from said inlet connection, said housing including a wall having a single closed continuous spiral grooved passage defined therein located at the separation between said inlet and said outlet connection, a filter extending across said spiral passage, said spiral passage communicating with said discharge connection and the opposite side of said filter communicating with said inlet connection, said discharge connection having a cannula communicating with the discharge passage therein.

15. A cannula according to claim 14, including an attachment having a bore therethrough communicating with said inlet passage and a cover having a closable portion overlying the bore of said attachment.

16. A cannula according to claim 14, wherein said filter housing comprises a relatively flat housing, said inlet and said outlet passages being located in axial alignment with said housing extending laterally to one side thereof, said housing having a groove defined therein forming a flow passage, a filter extending over said groove between the flow passage and said inlet, said flow passage communicating with the outlet of said housing.

* * * * *